US009522259B2

(12) United States Patent
Hernández Herrero et al.

(10) Patent No.: US 9,522,259 B2
(45) Date of Patent: Dec. 20, 2016

(54) INSTRUMENT FOR INSERTING A SUPPOSITORY

(75) Inventors: Gonzalo Hernández Herrero, Madrid (ES); Celestino Ronchi, Milan (IT); Mauro Citterio, Merate (IT); Lucas Sigman, Alcobendas (ES); Brett Mooney, Leon (ES)

(73) Assignee: LABORATORIOS LEÓN Farma, S.A., Villaquilambre (ES)

( * ) Notice: Subject to any disclaimer, the term of this patent is extended or adjusted under 35 U.S.C. 154(b) by 56 days.

(21) Appl. No.: 14/237,031

(22) PCT Filed: Aug. 3, 2012

(86) PCT No.: PCT/EP2012/065270
§ 371 (c)(1),
(2), (4) Date: Feb. 4, 2014

(87) PCT Pub. No.: WO2013/020922
PCT Pub. Date: Feb. 14, 2013

(65) Prior Publication Data
US 2014/0171882 A1    Jun. 19, 2014

(30) Foreign Application Priority Data

Aug. 5, 2011  (EP) .................................. 11382273

(51) Int. Cl.
*A61M 31/00*     (2006.01)
*A61F 13/26*     (2006.01)
*A61M 5/50*      (2006.01)

(52) U.S. Cl.
CPC .......... *A61M 31/007* (2013.01); *A61F 13/266* (2013.01); *A61M 5/502* (2013.01); *F04C 2270/0421* (2013.01)

(58) Field of Classification Search
CPC ................ A61M 5/5013; A61M 5/502; A61M 2005/5026; A61M 2005/5033; A61M 31/007; A61F 13/266
(Continued)

(56) References Cited

U.S. PATENT DOCUMENTS 3,667,465 A  *  6/1972  Voss ..................... A61M 31/007
                                                  604/197
3,934,586 A  *  1/1976  Easton ................. A61M 5/5013
                                                  222/47

(Continued)

FOREIGN PATENT DOCUMENTS

DE    3031408 A1    3/1982
FR    2610831 A1    8/1988
WO    WO03101525 A1    12/2003

OTHER PUBLICATIONS

International Search Report and the Written Opinion of the International Searching Authority Search Report Application No. PCT/EP2012/065270 issued by EPO, Rijswijk, Netherlands dated Sep. 7, 2012.

*Primary Examiner* — Kevin C Sirmons
*Assistant Examiner* — William Carpenter
(74) *Attorney, Agent, or Firm* — Peter B. Scull; Hamilton, DeSanctis & Cha LLP (57) ABSTRACT

An instrument for inserting a suppository including a tube, having a first end adapted to receive the suppository and a second end, a plunger disposed in the tube and moveable therein to eject the suppository from the first end by causing an action of pushing the suppository from behind. Retaining tongues are splayed outwards for ejection of the suppository in response to movement of the plunger in the tube, via contacting cooperation between at least one part of the plunger and at least one part of the tube. Securement mechanism secure the plunger in the tube at first position in (Continued)

which the suppository is retained in the first end of the tube, while allowing a user to move the plunger to actuate the instrument, and to secure the plunger in the tube at a second position which is only achievable after the plunger has been moved to eject the suppository.

14 Claims, 5 Drawing Sheets

(58) Field of Classification Search
USPC .................................................. 604/110, 220
See application file for complete search history.

(56) References Cited

U.S. PATENT DOCUMENTS

| | | | | |
|---|---|---|---|---|
| 4,367,738 | A | * | 1/1983 | Legendre ............ A61M 5/5013 604/110 |
| 4,767,413 | A | * | 8/1988 | Haber .................. A61M 5/326 604/198 |
| 4,826,483 | A | * | 5/1989 | Molnar, IV ......... A61M 5/5013 604/110 |
| 4,990,136 | A | * | 2/1991 | Geria .................. A61M 31/007 604/59 |
| 5,263,934 | A | * | 11/1993 | Haak .................... A61M 5/322 604/110 |
| 5,634,903 | A | * | 6/1997 | Kurose ................ A61M 5/315 604/110 |
| 5,860,946 | A | | 1/1999 | Hofstatter |
| 6,086,566 | A | * | 7/2000 | Arnissolle ........... A61M 5/3202 604/192 |
| D718,857 | S | * | 12/2014 | Hernandez Herrero ..... D24/141 |
| 2003/0158510 | A1 | * | 8/2003 | Huang ................ A61M 31/007 604/15 |
| 2003/0195459 | A1 | | 10/2003 | Shippert |
| 2006/0217652 | A1 | | 9/2006 | Heuer et al. |
| 2008/0167625 | A1 | * | 7/2008 | Earhart ................ B29C 59/021 604/218 |
| 2010/0286609 | A1 | * | 11/2010 | Mahurkar ........... A61M 5/3234 604/110 |

* cited by examiner

INSTRUMENT FOR INSERTING A SUPPOSITORY

PRIORITY

This application is the national stage entry of PCT/EP2012/065270, filed 3 Aug. 2012 and published on 14 Feb. 2013 as WO 2013/020922, which claims the benefit of EP 11382273.8 filed 5 Aug. 2011.

TECHNICAL FIELD

An instrument for inserting a suppository is disclosed herein.

BACKGROUND

WO 03101525 A1 discloses a suppository applicator consisting of a piston arranged to be displaced within a tubular sleeve in a suppository applicator when an end piece of the piston is provided with a force being opposed by means of an equally large and oppositely directed counter-force being applied to a finger grip. The piston and the tubular sleeve are attached to each other by means of two elastic and resilient elements placed on the outside of said piston. When force applied to the end piece of the piston ceases, the piston returns to the position that the piston held before applying the force.

FR 2610831 A1 discloses a syringe for inserting suppositories, whatever the size, in a hygienic manner, and also to prevent the suppository from melting during handling, in particular in hot countries. It consists of a cylindrical plastic tube, into which a pusher is inserted, provided with a rod which is used for guiding the suppository trapped by three clamps fixed to the end of the tube. The apparatus is in particular intended for hospitals, clinics and individuals, in particular large persons for whom fitting suppositories presents the greatest difficulty.

DE 3031408 A1 discloses an inserting device, in particular for suppositories, characterized in that the device comprises a sleeve-shaped housing, wherein the piston is movingly guided, having an actuating element at one end and the operating element at the opposite end of the housing, wherein a portion of the inner housing wall has a cup-like receiving area for a suppository and wherein the length of said receiving area is variable by the piston displacement.

U.S. Pat. No. 5,860,946, the disclosure of which is incorporated herein by reference, describes an instrument for inserting a suppository, comprising a tube with a first end which is adapted for receiving a suppository and a second end through which a plunger is inserted in the tube. The first end defines the front or distal end of the instrument in the direction of insertion, and the second end defines the rear or proximal end. The plunger has corresponding first and second ends, the first end having a circular cross section and two axially spaced circumferential flanges and the second end adapted to project from the second end of the tube before manual actuation of the instrument by the user to eject the suppository from the first end of the tube. The first end of the tube has an inwardly extending shoulder which engages between said flanges of the plunger, this engagement having the purpose of holding the plunger in the tube, with the second end projecting form the tube as described above, before the suppository is ejected. The first end of the plunger is divided in to a number of sectors by radial slots.

Prior to ejection, the suppository is held in the first end of the tube of the prior art device by opposite resilient tongues having, in walls facing each other, recesses mating the outer contour of the suppository.

The user manually actuates the instrument by pushing the projecting second end of the plunger fully into the tube, which causes the plunger to disengage from its position held by the shoulder and the flanges and move forwards in the tube to push the suppository out of the front end of the tube.

Experience has shown that the prior art device has a number of disadvantages. For example, the suppository can become damaged by scraping against the tongue walls of the tube in the ejection process. Another disadvantage is that the user has no way to know with relative certainty that the suppository has been ejected correctly—for example in the vicinity of the cervix as far as an intravaginal applicator is concerned. The holding cooperation between the shoulder and the flanges, which provides the pre-actuation holding of the plunger, is weak and the plunger can quite easily be prematurely pushed forwards in the tube to eject the suppository. After actuation the plunger can freely move forwards and backwards in the tube and can even be returned to the held condition.

The present instrument aims to at least partially overcome these problems or at least to provide an alternative instrument for inserting a suppository.

SUMMARY

In a first aspect an instrument is provided for inserting a suppository, including:
  a tube, having a first end adapted to receive the suppository and defining a forward end of the instrument in use, and a second end defining a rearward end of the instrument in use, and
  a plunger disposed in the tube and moveable therein to eject the suppository from the forward end of the instrument by causing an action of pushing the suppository from behind,
  wherein
  the first end of the tube has an internal configuration which defines a space for receiving the suppository,
  at least one member is provided at the first end of the tube which is moveable between a first condition in which the suppository is thereby prevented from exiting the tube and a second condition in which the suppository is substantially not prevented from exiting the tube, and
  the said movement of the member(s) from the first condition to the second condition thereof is in response to movement of the plunger in the tube and the said movement of the member(s) takes place via contacting cooperation between at least one part of the plunger and at least one part of the tube.

The instrument may be provided with a securement mechanism to (a) secure the plunger in the tube at a first position, prior to actuation of the instrument, in which the suppository is retained in the space defined in the first end of the tube, while allowing a user to manually release the securement mechanism to move the plunger to actuate the instrument, and to (b) secure the plunger in the tube at a second position which is only achievable after the plunger has been moved to eject the suppository from the forward end of the instrument.

The contacting cooperation between at least one part of the plunger and at least one part of the tube may, for example, be obtained by direct contacting cooperation between a cooperating shoulder of the front end of the plunger and an internal tapering face of the at least one member.

The arrangement may, for example, be such that in use the suppository does not contact the at least one member to cause movement thereof.

The at least one member may, for example, include a pair of opposed, resiliently mutually outwardly flexible, forwardly directed tongues of the wall of the tube at the first end thereof. The tongues may be provided with mutually inwardly directed lips.

The parts may, for example, be arranged so that the movement between the first and the second condition of the member(s) starts immediately before the suppository is pushed from behind.

This instrument effectively solves the problem of possible damage to the suppository by scraping against the internal walls of the front end of the tube, as found in the prior art. The movement of the at least one member to allow the suppository to exit the tube takes place via contacting cooperation between at least one part of the plunger and at least one part of the tube, that is, without the need for the suppository itself to play a part in moving the member(s) to allow the suppository to exit the tube. Furthermore, by preferably arranging the moving parts so that the movement between the first and the second condition of the member(s) starts immediately before the suppository is pushed from behind, the suppository cannot fall out of the tube too early. It is not excluded that the suppository may mildly touch the at least one moveable member, or may encounter other mild resistance from the at least one moveable member, when ejected past it, provided always that the second condition of the moveable member(s) offers substantially less resistance to ejection than the first condition, and that the movement between the first and the second condition of the member(s) takes place via contacting cooperation between at least one part of the plunger and at least one part of the tube.

In a second aspect an instrument is provided for inserting a suppository, which instrument includes:
  a tube, having a first end adapted to receive the suppository and defining a forward end of the instrument in use, and a second end defining a rearward end of the instrument in use, and
  a plunger disposed in the tube and moveable therein to eject the suppository from the forward end of the instrument by causing an action of pushing the suppository from behind,
  wherein
  the first end of the tube has an internal configuration which defines a space for receiving the suppository,
  a securement mechanism is provided to (a) secure the plunger in the tube at a first position, prior to actuation of the instrument, in which the suppository is retained in the space defined in the first end of the tube, while allowing a user to manually release the securement mechanism to move the plunger to actuate the instrument, and to (b) secure the plunger in the tube at a second position which is only achievable after the plunger has been moved to eject the suppository from the forward end of the instrument.

This instrument effectively solves the problem of the user not being certain that the instrument has been correctly actuated, as found in the prior art. The plunger of the actuated instrument is secured in a position which is only achievable after the plunger has been moved to eject the suppository from the forward end of the instrument. Furthermore, by arranging the securement mechanism so that the act of manual release requires a specific manual action such as pushing the plunger into the tube, and/or application of finger or thumb pressure on a part of the instrument, and/or by arranging for that act of manual release to be accompanied by a characteristic signal such as a click or other sound, the user has complete certainty during use of the instrument as to what is happening at the front end. The securement of the plunger in the tube at the second position may be manually released to allow the plunger to be drawn back out of the tube to reset the instrument.

The first and second aspects may conveniently be used together, although they do not have to be.

The details, examples and preferences provided below in relation to any particular one or more of the stated aspects, apply equally to all aspects.

DETAILED DESCRIPTION

The general operation of the instrument is quite similar to that of the prior art instrument described above.

For example, the tube and plunger may be formed in any suitable material, such as moulded plastics. Suitable moulding methods include, for example, blow moulding, compression moulding, extrusion moulding and injection moulding.

Particular points of difference from the prior art instrument are described below.

The tube may have any internal transverse cross-sectional shape, for example circular, oval, polygonal, rectangular. The plunger may suitably has a corresponding external transverse cross-sectional shape, to be snugly retained in the tube and slidable therein.

We have found it convenient to use a tube which has an internal shape that limits the freedom of rotational movement of a correspondingly shaped plunger in the tube. For example, the tube may have a rectangular internal transverse cross-sectional shape, having two long sides and two short sides. A corresponding plunger can be disposed in the tube in only two orientations with no rotational freedom.

As far as the first is concerned, this has the advantage that the member(s) provided at the first end of the tube can be one or more tongue, for example forwardly projecting and forming part of the wall defining the space for receiving the suppository, most suitably a pair of such tongues at opposite sides of the space to overlie the small dimension of a typical round tablet-shaped suppository.

The one or more tongue can suitably be resiliently outwardly flexible in response to movement of the plunger in the tube, such that in the outwardly flexed condition the suppository can exit the tube when pushed by the plunger from behind. The one or more tongue can suitably be provided with an internally directed lip to assist retention of the suppository behind the lip in the space defined at the first end of the tube, before ejection, provided that in the second condition of the one or more tongue the suppository is substantially free to exit the instrument.

The tube member(s) may be moved by any suitable mechanism or method. Cooperating formation(s) on internal face(s) of the member(s) and on the exterior of the plunger may, for example, serve to move the member(s) outwardly in response to forward movement of the plunger in the tube. Suitable formations include cooperating angled or tapered shoulders and projections on the parts, as will be readily understood by the reader.

As far as the second aspect is concerned, the use of cross-sectional configurations of the tube and plunger that restrain rotational movement of the plunger in the tube has the advantage that manually operable parts of the securement mechanism can be provided on the external surface of the tube, for example at or towards the second end of the tube, and any cooperating parts on the plunger can be easily aligned with the external parts of the tube simply on inserting the plunger into the tube, all possible rotational orientations for the plunger within the tube being workable in this respect.

For example, the securement mechanism may include parts provided externally of the tube on opposite sides of the tube. Such parts may suitably be operable by pushing the plunger into the tube, where this action is not prevented by any stop or the like, and/or a squeezing action between thumb and fingers of the user. For example, the manual release of the securement mechanism in the first position may be by pushing the plunger into the tube. The manual release of the securement mechanism in the second position to reset the instrument may be by a squeezing action between thumb and fingers of the user.

The manually operable parts may include finger grip depressions, sprung projections such as buttons or levers, and others as are conventional in manually operable release mechanisms, including any combination thereof.

The manner of use of the instrument is largely similar to the use of the prior art instrument mentioned above. Briefly, the suppository is manually located in the space at the first (forward) end of the tube, taking care not to damage the suppository. The plunger is then loaded into the tube from the second (rearward) end.

With the instrument according to the first aspect, pushing of the plunger forwards will splay the tongue(s) or other moveable member(s) at the front end of the tube, allowing release of the suppository after the instrument has been located correctly for administration.

With the instrument according to the second aspect, at the correct first position the securement mechanism will secure the plunger in the tube and the instrument is ready for use. When the instrument is correctly located for administration, the user pushes the plunger, which action releases the securement mechanism and allows the plunger to go fully into the tube. When the suppository is ejected, the securement mechanism secures the plunger in the second position, typically the position which has been achieved by the plunger at the point of full insertion of the plunger into the tube. The user now knows that the suppository has been ejected and can withdraw the instrument. To reset the instrument for reuse the securement mechanism can be released by manual action, to allow the plunger to be withdrawn from the tube.

BRIEF DESCRIPTION OF THE DRAWINGS

For better understanding, but without limitation, an embodiment of the present instrument will be further described with reference to the following drawings wherein.

DETAILED DESCRIPTION OF THE DRAWINGS

Referring to the drawings, in which like parts are designated alike, there is shown an instrument for inserting a suppository, for example an intravaginal suppository in round tablet form. The illustrated embodiment embodies both aspects.

In general terms, the instrument includes a tube 1, having a first end 2 adapted to receive the suppository 3 and defining a forward end of the instrument in use, and a second end 4 defining a rearward end of the instrument in use, and a plunger 5 disposed in the tube 1 and moveable therein to eject the suppository 3 from the forward end of the instrument by causing an action of pushing the suppository from behind. The tube 1 and the plunger 5 have a generally rectangular transverse cross-section and the respective cross-sectional dimensions and shapes of the tube 1 and plunger 5 are complementary so that the plunger 5 fits snugly and slidably in the tube 1 with no rotation.

The first end 2 of the tube 1 has an internal configuration which defines a generally rectangular space 6 for receiving the suppository 3.

A pair of resiliently outwardly flexible members in the form of forwardly directed tongues 7, 7' is provided at the first end 2 of the tube 1 and disposed to opposite sides of the rectangular space 6 to define the short sides of that rectangular space 6.

Figure 1:
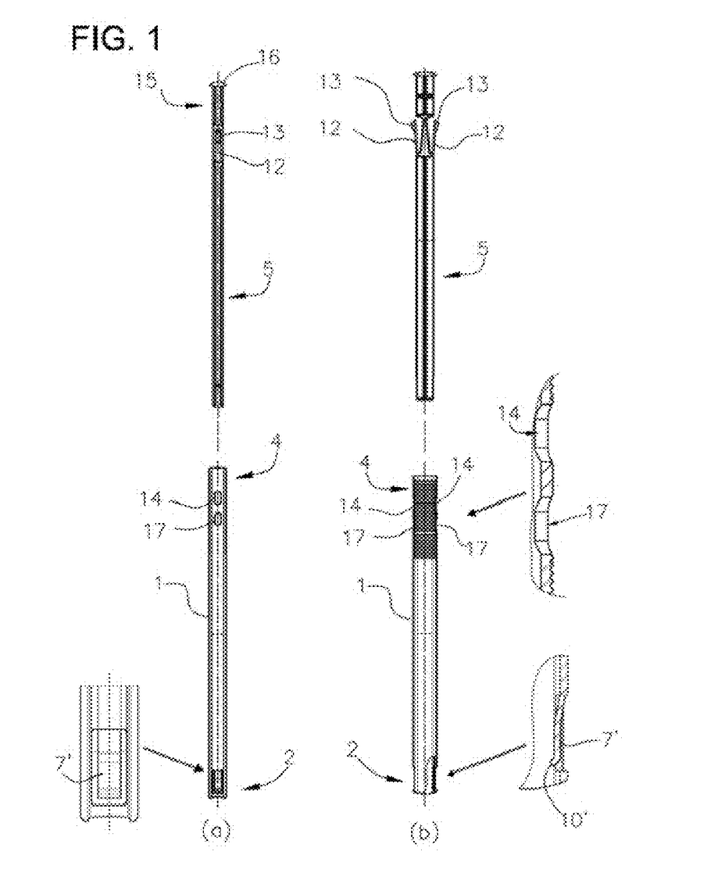
FIG. 1 shows an exploded side view of an instrument for inserting a suppository (a) from a first side and (b) from the orthogonal side, three regions also shown enlarged.
Figure 2:
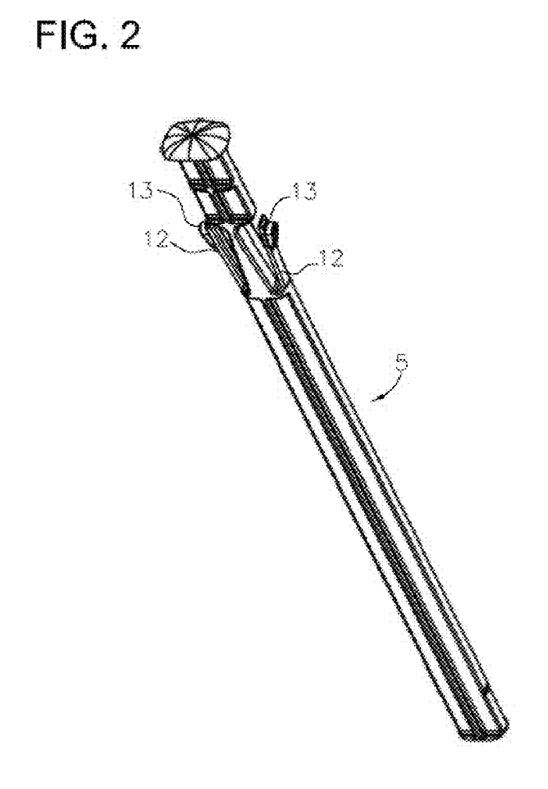
FIG. 2 shows a perspective view of the plunger part of the instrument of FIG. 1.
Figure 3:
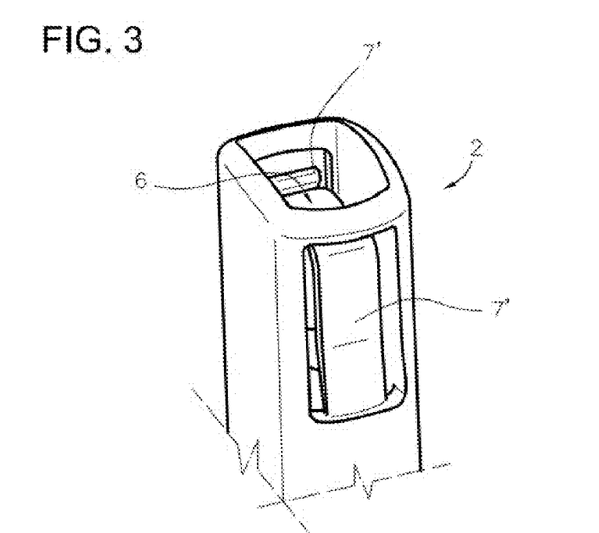
FIG. 3 shows a perspective view of the front end of the tube part of the instrument of FIG. 1.
Figure 4:
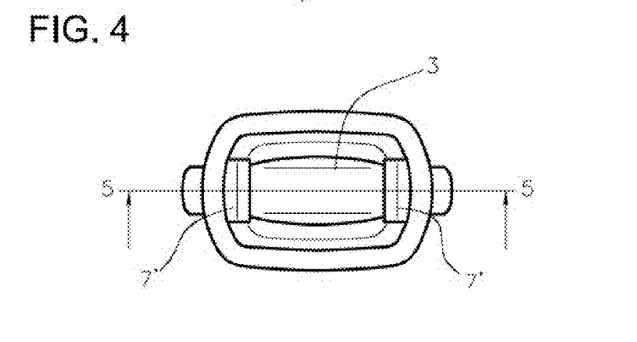
FIG. 4 shows a front view of the part shown in FIG. 3, with a suppository in place.
Figure 5:
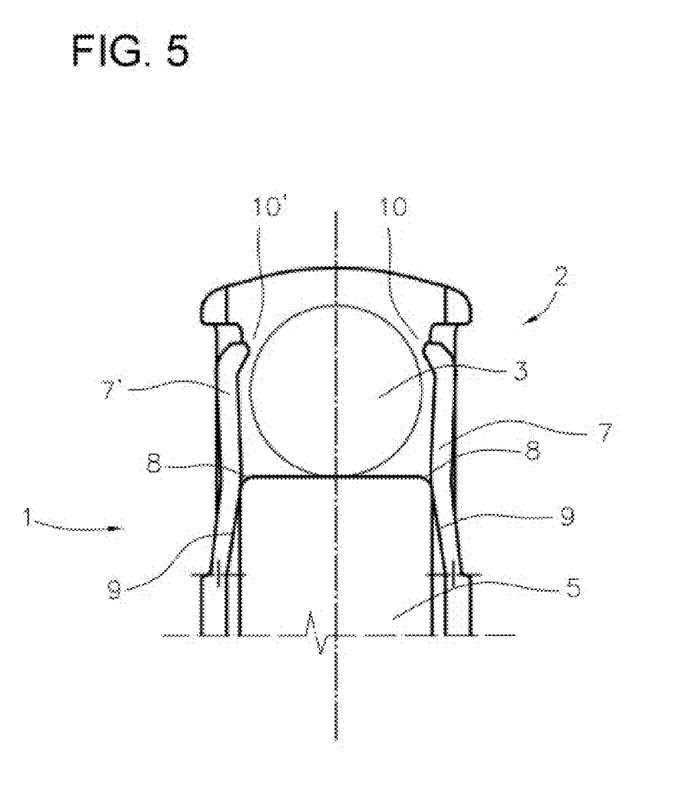
FIG. 5 shows a longitudinal cross-section along the line 5-5 in FIG. 4, looking in the direction of the arrows.
Figure 6:
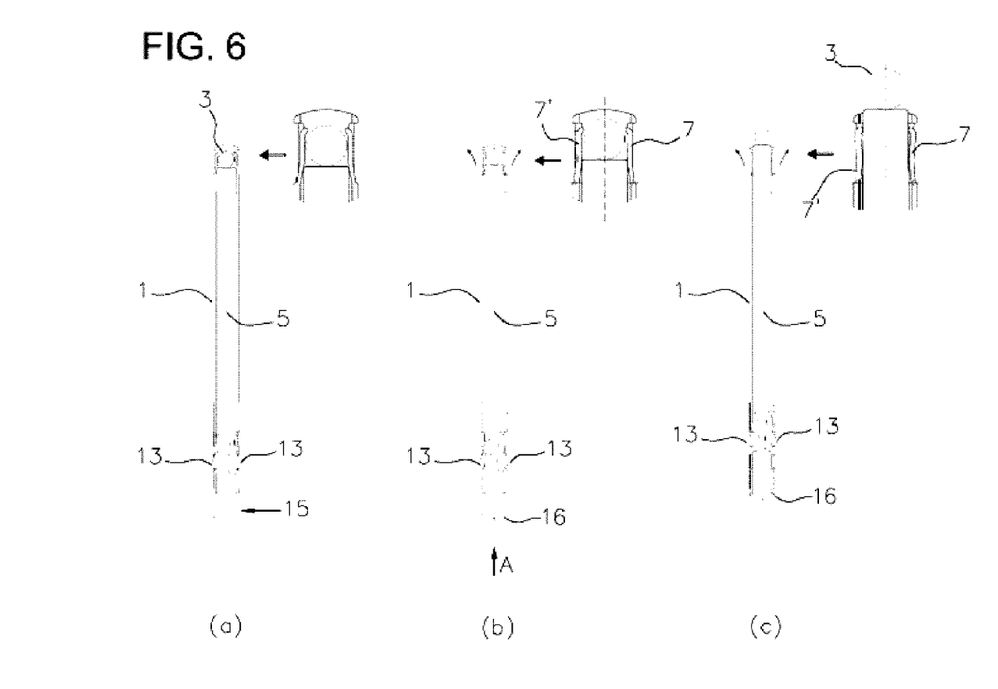
FIG. 6 shows in longitudinal cross-section the assembled instrument of FIGS. 1 to 5 in the three phases of operation (a) set for use, (b) part-way through pushing-in of the plunger, with the front end tongues beginning to splay, and (c) in the final condition after ejection of the suppository, in each case with the front end portion shown in enlarged view for clarity.

The pair of opposed tongues 7, 7' is resiliently moveable between a first condition (shown in FIGS. 3, 4 and 6(*a*)) in which the suppository 3 is prevented from exiting the tube and a second condition (shown in FIG. 6(*c*)) in which the suppository 3 is substantially not prevented from exiting the tube. In the intermediate condition (shown in FIGS. 5 and 6(*b*)), a direct contacting cooperation is established between a cooperating shoulder 8 of each short side of the front end of the rectangular plunger 5 and an internal tapering face 9 of the relevant one of the pair of opposed tongues 7, 7'. This direct contacting cooperation, which is not dependent on any action of the suppository 3 to splay the tongues 7, 7' outwards, continues because of the configuration of the shoulders 8 and the tapers 9 as the plunger 5 is pushed further into the tube 1 on actuating the instrument, that is, in going from the condition shown in FIG. 6(*b*) to the condition shown in FIG. 6(*c*).

The pair of opposed tongues 7, 7' is provided with internally directed lips 10, 10' which assist in preventing the suppository 3 from exiting the tube until the tongues 7, 7' have been splayed to a suitable extent.

A securement mechanism is provided to secure the plunger 5 in the tube 1 at a first position, prior to actuation of the instrument, in which the suppository 3 is retained in the space 6 defined in the first end 2 of the tube 1, while allowing a user to manually release the securement mechanism by pushing the plunger 5 to actuate the instrument. The securement mechanism in the illustrated embodiment include a pair of mutually outwardly splayed, rearwardly directed, and mutually inwardly resiliently deformable, arms 12, provided on the shaft of the plunger 5, and each arm having at its free rearward end outwardly directed formations 13 which provide in each case a surface that tapers inwards in the forward direction only, but in the rearward direction has a shoulder after the tapering surface.

These formations 13 are arranged to snap into a first pair of corresponding apertures 14 provided in the wall of the tube 1, to cause the plunger 5 to be releasably retained at the desired first position prior to actuation of the instrument, as shown in FIG. 6(*a*).

This enables the plunger to be releasably retained in the tube in the correct position prior to actuation, with the suppository in the position shown in FIGS. 4 and 6(*a*). As shown in FIG. 6(*a*), the rearward end 15 of the plunger 5 projects from the tube 1 when the plunger 5 is in this position.

To actuate the instrument from this condition, the plunger 5 is pushed fully into the tube, in the direction of the arrow A in FIG. 6(*b*). The tapering surfaces of the formations 13 slide over the rims of the apertures 14 so that the arms 12 flex inwardly offering no or only little resistance to the pushing of the plunger. As shown by the small arrows at the front end of the instrument illustrated in FIG. 6(*b*), the pushing of the plunger 5 fully into the tube 1 causes the tongues 7, 7' to splay mutually outwards, in response to the contacting cooperation between the shoulders 8 and the tapering surfaces 9 as described above. The front face of the plunger 5 thus can push the suppository 3 from behind, without substantial resistance from the tongues 7, 7', so that the suppository is ejected from the front end of the tube as shown in FIG. 6(*c*).

When the suppository 3 is ejected, that is, the plunger 5 is fully pushed into the tube 1, a circumferential stop flange 16 provided on the rear end of the plunger 5 abuts the rear end of the tube to limit the movement, as shown in FIG. 6(*c*).

Further, at this point the formations 13 snap into a second pair of corresponding apertures 17 provided in the wall of the tube 1, to cause the plunger to be retained at this second, actuated, position, as shown in FIG. 6(*c*). The securement of the plunger at the fully inserted position in the tube 1 is thus indicative to the user that the suppository has been ejected. The fact that the plunger was consciously moved from the first position of releasable retention to the second position of full actuation, with corresponding snap sounds from the arms 12 and formations 13 engaging into the apertures 17, provides certainty that the instrument was properly actuated.

To reset the instrument for next use, the user may squeeze the arms 12 together and retract the plunger 5 from the tube 1.

The foregoing broadly describes the present instrument without limitation. Variations and modifications as will be readily apparent to those skilled in the art are intended to be included in the scope of the present disclosure as defined by the following claims.

The invention claimed is:

1. A combination including an instrument for inserting a suppository, the combination comprising:
   a suppository;
   a tube, having a first end configured to receive the suppository and defining a forward end of the instrument in use, and a second end defining a rearward end of the instrument in use, and
   a plunger disposed in the tube and movable therein to eject the suppository from the forward end of the instrument by causing an action of pushing the suppository from behind,
   wherein
   the first end of the tube has an internal configuration which defines a space for receiving the suppository,
   at least one movable member is provided at the first end of the tube, the at least one movable member being configured to be disposed in relative first and second conditions whereby the at least one movable member is configured to be engaged by the plunger to move between the first condition in which the suppository is thereby prevented from exiting the tube and the second condition in which the suppository is substantially not prevented from exiting the tube, and
   the movement of the at least one movable member from the first condition to the second condition thereof is in response to engagement with and movement of the plunger in the tube and the movement of the at least one movable member takes place via contacting cooperation between at least one part of the plunger and at least one part of the tube;
   wherein the contacting cooperation between at least one part of the plunger and at least one part of the tube is obtained by direct contacting cooperation between a cooperating shoulder of the front end of the plunger and an internal tapering face of the at least one movable member; and,
   further comprising a securement mechanism to (a) secure the plunger in the tube at a first position, and to (b) secure the plunger in the tube at a second position;
   wherein the securement mechanism comprises at least one outwardly splayed, rearwardly directed, and inwardly resiliently deformable arm provided on the shaft of the plunger, and having at its free rearward end an outwardly directed formation which provides a surface that tapers inwards in the forward direction only, and in the rearward direction has a shoulder after the tapering surface, the formation being arranged to snap into a corresponding first aperture provided at a first position in the wall of the tube for providing the securement mechanism at the first position and a corresponding second aperture provided at a second position in the wall of the tube for providing the securement mechanism at the second position.

2. The instrument of claim 1, wherein the securement mechanism in (a) to secure the plunger in the tube at a first position, is prior to actuation of the instrument, in which the suppository is retained in the space defined in the first end of the tube, while allowing a user to manually release the securement mechanism to move the plunger to actuate the instrument, and in (b) to secure the plunger in the tube at a second position is only achievable after the plunger has been moved to eject the suppository from the front end of the instrument.

3. The instrument of claim 2, wherein the securement mechanism is releasable in the first position by the act of manually pushing the plunger into the tube from the first position to the second position.

4. The instrument of claim 2, wherein the securement mechanism is releasable in the second position to reset the instrument.

5. The instrument of claim 1, at least one of:
   wherein in the second condition in which the suppository is substantially not prevented from exiting the tube, the at least one movable member is not in contact with the suppository; or,
   wherein the arrangement is such that in use the suppository does not contact the at least one movable member to cause movement thereof.

6. The instrument of claim 1, wherein the at least one movable member comprises a pair of opposed, resiliently mutually outwardly flexible, forwardly directed tongues of the wall of the tube at the first end thereof.

7. The instrument of claim 6, wherein the tongues comprise mutually inwardly directed lips.

8. The instrument of claim 1, wherein the parts are arranged so that the movement between the first and the second condition of the at least one movable member starts immediately before the suppository is pushed from behind.

9. The instrument of claim 1, wherein the suppository is received in the space at the first end of the tube.

10. The instrument of claim 1, wherein the contacting cooperation between at least one part of the plunger and at least one part of the tube is obtained by direct contacting cooperation between a cooperating front part of the plunger and an internal part of the at least one movable member.

11. A combination including an instrument for inserting a suppository, the combination comprising:
 a suppository;
 a tube, having a first end configured to receive the suppository and defining a forward end of the instrument in use, and a second end defining a rearward end of the instrument in use, and
 a plunger disposed in the tube and movable therein to eject the suppository from the forward end of the instrument by causing an action of pushing the suppository from behind,
 wherein
 the first end of the tube has an internal configuration which defines a space for receiving the suppository,
 a securement mechanism is provided to (a) secure the plunger in the tube at a first position, prior to actuation of the instrument, in which the suppository is retained in the space defined in the first end of the tube, while allowing a user to manually release the securement mechanism to move the plunger to actuate the instrument, and to (b) secure the plunger in the tube at a second position which is only achievable after the plunger has been moved to eject the suppository from the forward end of the instrument;
 wherein the securement mechanism comprises at least one outwardly splayed, rearwardly directed, and inwardly resiliently deformable arm provided on the shaft of the plunger, and having at its free rearward end an outwardly directed formation which provides a surface that tapers inwards in the forward direction only, and in the rearward direction has a shoulder after the tapering surface, the formation being arranged to snap into a corresponding first aperture provided at a first position in the wall of the tube for providing the securement mechanism at the first position and a corresponding second aperture provided at a second position in the wall of the tube for providing the securement mechanism at the second position;
 and, further comprising:
 at least one movable member is provided at the first end of the tube, the at least one movable member being configured to be disposed in relative first and second conditions whereby the at least one movable member is configured to be engaged by the plunger to move between the first condition in which the suppository is thereby prevented from exiting the tube and the second condition in which the suppository is substantially not prevented from exiting the tube, and
 the movement of the at least one movable member from the first condition to the second condition thereof is in response to engagement with and movement of the plunger in the tube and the movement of the at least one movable member takes place via contacting cooperation between at least one part of the plunger and at least one part of the tube;
 wherein the contacting cooperation between at least one part of the plunger and at least one part of the tube is obtained by direct contacting cooperation between a cooperating front part of the plunger and an internal part of the at least one movable member.

12. The instrument of claim 11, wherein the securement mechanism is releasable in the first position by the act of manually pushing the plunger into the tube from the first position to the second position.

13. The instrument of claim 11, wherein the securement mechanism is releasable in the second position to reset the instrument.

14. The instrument of claim 11, wherein the suppository is received in the space at the first end of the tube.

* * * * *